United States Patent
Belliere-Baca et al.

(10) Patent No.: US 12,162,823 B2
(45) Date of Patent: Dec. 10, 2024

(54) PROCESS FOR PREPARING A COMPOUND OF FORMULA RSH BY HYDROSULFURIZATION

(71) Applicant: ADISSEO FRANCE S.A.S., Antony (FR)

(72) Inventors: Virginie Belliere-Baca, Millery (FR); Virginie Harle, Senlis (FR); Sylvette Brunet, Sevres Anxaumont (FR); Olivier Peruch, Lyons (FR)

(73) Assignee: ADISSEO FRANCE S.A.S., Antony (FR)

( * ) Notice: Subject to any disclaimer, the term of this patent is extended or adjusted under 35 U.S.C. 154(b) by 511 days.

(21) Appl. No.: 17/423,267

(22) PCT Filed: Jan. 16, 2020

(86) PCT No.: PCT/FR2020/050060
§ 371 (c)(1),
(2) Date: Jul. 15, 2021

(87) PCT Pub. No.: WO2020/148510
PCT Pub. Date: Jul. 23, 2020

(65) Prior Publication Data
US 2022/0127222 A1  Apr. 28, 2022

(30) Foreign Application Priority Data
Jan. 18, 2019 (FR) ..................... 19/00463

(51) Int. Cl.
| | | |
|---|---|---|
| *C07C 319/06* | (2006.01) | |
| *B01J 21/04* | (2006.01) | |
| *B01J 23/00* | (2006.01) | |
| *B01J 23/10* | (2006.01) | |
| *C07C 319/08* | (2006.01) | |
| *C07C 319/14* | (2006.01) | |

(52) U.S. Cl.
CPC ............ *C07C 319/06* (2013.01); *B01J 21/04* (2013.01); *B01J 23/002* (2013.01); *B01J 23/10* (2013.01); *C07C 319/08* (2013.01); *C07C 319/14* (2013.01); *C07C 2521/04* (2013.01); *C07C 2523/10* (2013.01)

(58) Field of Classification Search
CPC ... C07C 319/08; C07C 319/14; C07C 319/06; B01J 21/04; B01J 23/10; B01J 23/04
See application file for complete search history.

(56) References Cited

U.S. PATENT DOCUMENTS

| | | | | |
|---|---|---|---|---|
| 2,514,300 A | * | 7/1950 | Laughlin | ............... C07C 319/08 568/71 |
| 4,302,605 A | | 11/1981 | Buchholz et al. | |
| 4,313,006 A | * | 1/1982 | Hager | ................. C07C 321/00 568/61 |
| 4,490,567 A | * | 12/1984 | Drake | ................... C07C 1/24 585/324 |
| 9,745,262 B2 | * | 8/2017 | Barth | .................. C07C 319/02 |
| 2007/0189955 A1 | * | 8/2007 | Larcher | ............... C01G 25/006 252/500 |

FOREIGN PATENT DOCUMENTS

| | | |
|---|---|---|
| CN | 1207958 A | 2/1999 |
| FR | 2773559 A1 | 7/1999 |
| JP | 2000167399 A | 6/2000 |
| JP | 2011126873 A | 6/2011 |
| JP | 5752921 B2 | 5/2015 |
| WO | 2013092129 A1 | 6/2013 |

OTHER PUBLICATIONS

Bermejo-Deval et al., "On the role of the alkali cations on methanol thiolation", Catal. Sci. Technol., 2017, 7, 4437.
Paskach et al., "Synthesis of Methanethiol from Methanol over Reduced Molybdenum Sulfide Catalysts Based on the Mo6S8 Cluster", Journal of Catalysis 211, 285-295 (2002) doi:10.1006/jcat.2002.3684.
Plaisance, Craig, "Zeolite and metal oxide catalysts for the production of dimethyl sulfide and methanethiol" (2005). LSU Master's Theses. 2430, 116 pages.
Craig P Plaisance et al, "Zeolite and Metal Oxide Catalysts for the Production of Dimethyl Sulfide and Methanethiol", Catalysis Letters, 2009, vol. 128, No. 3-4, pp. 449-458, XP019672020.
International Search Report issued May 6, 2020 re: Application No. PCT/FR2020/050060, pp. 1, citing: Plaisance et al. "Zeolite and Metal Oxide . . . " and Ziolek et al. "Influence fo hydrogen . . . ".
M. Ziolek et al, "Influence of hydrogen sulfide adsorption on the catalytic properties of metal oxides", Journal of Molecular Catalysis A: Chemical 97, Mar. 21, 1995, vol. 97, No. 1, pp. 49-55, XP055627164.

* cited by examiner

*Primary Examiner* — Rosalynd A Keys
(74) *Attorney, Agent, or Firm* — CANTOR COLBURN LLP

(57) ABSTRACT

A method for preparing a compound of formula RSH where R represents an alkyl group, by gas-phase catalytic reaction of hydrogen sulfide with a compound of formula ROH, in the presence of a solid catalyst, according to which method the reaction is performed in the presence of a catalyst which includes one or several pure or mixed rare-earth oxide(s), one or several pure or mixed rare-earth sulfide(s), or one or several pure or mixed rare-earth oxysulfide(s). When the rare earth is lanthanum, the catalyst is a mixed oxide of lanthanum and of at least one metal selected from rare earths or not and when the rare earth is cerium, the catalyst is supported on an alumina.

5 Claims, No Drawings

PROCESS FOR PREPARING A COMPOUND OF FORMULA RSH BY HYDROSULFURIZATION

TECHNICAL FIELD

The disclosure concerns a method for gas-phase catalytic hydrosulfurization of an alcohol into the corresponding thiol. More particularly, it is described for the production of methanethiol from methanol and hydrogen sulfide, without its scope being restricted thereto.

BACKGROUND

The hydrosulfurization reaction of methanol into methanethiol through a gas-phase catalytic route is known. Usually, this is carried out in the presence of a catalyst based on an oxide of tungsten and of an alkaline metal supported on an alumina, as described for example in the patent WO2013092129A1.

Nevertheless, there are some researches covering alternative catalysts in the literature. Thus, the works of Plaisance and Dooley (Catalysis Letters, 2009, 128, 449-458) describe the use of catalysts based on different oxides of metals such as tungsten ($WO_3$), lanthanum ($La_2O_3$) or titanium ($TiO_2$) supported on various solids. Amongst all of these, tungsten oxide is most active one. These works highlight the fact that the activity of each of the tested catalysts depends on different parameters and that it is hard to determine optimum conditions that are common to several catalysts. In addition, with the catalyst based on lanthanum oxide supported on alumina ($La_2O_3/Al_2O_3$), a high methanol conversion is obtained, but this is accompanied with a very low methanethiol selectivity, which makes this catalyst incompatible with an application on an industrial scale.

Moreover, Ziolek et al. (Journal of Molecular Catalysis A: Chemical, 1997, 97, 49-55) describe the influence of the adsorption of hydrogen sulfide during the hydrosulfurization reaction of methanol in the presence of different catalysts based on oxides of magnesium (MgO), titanium ($TiO_2$), zirconium ($ZrO_2$), cerium ($CeO_2$) and aluminum ($Al_2O_3$). In particular, the authors have observed the highest adsorption of hydrogen sulfide on ceria and have correlated this phenomenon with increased methanethiol and dimethyl sulfide selectivities. Nevertheless, with an average methanol conversion, this catalyst generates a large amount of methane, at the expense of the methanethiol selectivity, such that methane becomes the predominant product of the reaction under some conditions.

SUMMARY

It turns out that, to date, there is still the need to develop conditions of a catalytic hydrosulfurization reaction of methanol in a gas phase, at the level of the catalyst as well as the parameters of the process, which features both a high methanol conversion rate and a great methanethiol selectivity and which reduces the production of non-recoverable by-products such as light compounds.

The disclosure provides a method that meets these requirements.

This method allows preparing a compound of formula RSH where R represents an alkyl group, by gas-phase catalytic reaction of hydrogen sulfide with a compound of formula ROH, in the presence of a solid catalyst, this catalyst comprising or consisting of one or several pure or mixed rare-earth oxide(s), one or several pure or mixed rare-earth sulfide(s), or one or several pure or mixed rare-earth oxysulfide(s), provided that when the rare earth is lanthanum, said catalyst is a mixed oxide of lanthanum and of at least one metal selected from rare earths and when the rare earth is cerium, said catalyst is supported.

It has been observed that using such a catalyst, the selectivity has been improved significantly in comparison with the catalysts described in the prior art, in particular by a decrease that could reach a magnitude of at least 40% of non-recoverable products such as carbon monoxide, carbon dioxide, methane, hydrogen and dimethyl ether. Thus, the main product is methanethiol, and the dimethyl sulfide constitutes the predominant secondary product. The latter may be skillfully recycled to be converted into methanethiol, thereby increasing the overall yield of the methanethiol process. In addition, thanks to this method, the reaction may be conducted over a wider range of temperatures generally lower than those of the known methods. More generally, this method has the advantage of being flexible and depending on the operational conditions such as the temperature, it is possible to direct the selectivity towards either product.

DETAILED DESCRIPTION OF THE DISCLOSURE

The method of the disclosure is described hereinafter in more details with features that may be considered alone or in combination(s) irrespective of the combination(s), and preferred implementation variants are provided.

Before this more detailed description, some terms used in the text are defined.

By rare earths, it should be understood the 15 lanthanides (lanthanum, cerium, praseodymium, neodymium, promethium, samarium, europium, gadolinium, terbium, dysprosium, holmium, erbium, thulium, ytterbium and lutetium), as well as scandium and yttrium.

According to the disclosure, the catalyst may be present in the form of an oxide (or oxide-hydroxide), sulfide or any intermediate form containing S and O that is called oxysulfide.

In the formulas defining the obtained or involved compounds, the term "alkyl" refers to a linear or branched hydrocarbon monovalent radical having from 1 to 20 atoms of carbon, advantageously from 1 to 6 atoms of carbon, such as methyl, ethyl, propyl, isopropyl, butyl, isobutyl, tert-butyl, pentyl, neopentyl, n-hexyl or a cyclic hydrocarbon monovalent radical having from 3 to 20 atoms of carbon, advantageously from 3 to 6 atoms of carbon, such as cyclopropyl, cyclohexyl, but without limitation to these radicals.

According to a method of the disclosure, the catalyst is selected from rare-earth oxides, hydroxides or oxide-hydroxides of rare earths and of at least one other metal that is not a rare earth. The catalyst may also be selected from mixed oxides (hydroxides or oxide-hydroxides) of rare earths and of at least one other metal that is not a rare earth. By mixed oxides, it should be understood an oxide based on one or several rare earth(s). The catalyst may also be selected from mixed sulfides of several rare earths, mixed sulfides of one or several rare earth(s) and of at least one other metal that is not a rare earth, oxysulfides of several rare earths, mixed oxysulfides of one or several rare earth(s) and of at least one other metal that is not a rare earth, and the mixtures of said mixed oxides, mixed sulfides and mixed oxysulfides. Preferably, said metal that is not a rare earth is zirconium.

In addition to the aforementioned oxides, sulfides and/or oxysulfides, the catalyst may also comprise one or several oxide(s) of metals other than rare earths.

In a variant of the disclosure, the catalyst is supported, advantageously on alumina, whether pretreated or not, which allows overcoming the plugging problems that might be observed in the presence of materials based on powdery rare earths.

As indicated before, the method of the disclosure is particularly interesting for the preparation of methanethiol by catalytic hydrosulfurization of methanol, but it may be suited for the obtainment of any compound RSH, where R is an alkyl as defined before.

Among suitable catalysts according to the disclosure, some combinations are selected because of their effectiveness. Thus, advantageously, the catalyst comprises or consists of mixed oxides of lanthanum, cerium, neodymium and zirconium; in this combination, the proportions of zirconium and cerium oxides are predominant compared to those of lanthanum and neodymium oxides.

According to the disclosure, there has also been developed a support allowing increasing the performances of the used catalysts. This support may be an alumina modified by potassium, with a potassium content comprised between 0.1% and 20% (m/m), preferably between 0.5% and 10%, and more preferably between 0.5% and 5%. In a variant of the disclosure, the use of ceria supported on an alumina modified this way is reported, in a range of supported cerium oxide contents comprised between 0.1% and 50% (m/m), preferably between 0.5% and 30% (m/m). This allows significantly increasing the methanethiol productivity of some catalysts used according to the disclosure, and in particular ceria, which, in the pure state, has a high methane selectivity, which has drawbacks in the production of methanethiol on an industrial scale.

In the method of the disclosure, the ratio between the hydrogen sulfide and the compound ROH will range from 0.5 to 20, preferably from 1 to 15, and more preferably from 1 to 10.

It has been indicated before that one amongst the benefits of the disclosure was to be able to enlarge the range of reaction temperatures. Thus, it may be performed at a temperature from 200° C. to 450° C., preferably from 250° C. to 420° C., and more preferably from 275° C. to 400° C., advantageously under a pressure comprised between 2 and 20 bar, preferably from 5 to 15 bar, and more preferably from 7 to 14 bar, and for a contact time of the compound ROH with the catalyst ranging from 0.1 second to 60 seconds.

Although the reaction is highly methanethiol selective, dimethyl sulfide may also be formed. It is then possible to further perform a catalytic conversion reaction of said dimethyl sulfide into methanethiol, according to techniques well known to those skilled in the art, to improve the yield of the methanethiol process even more.

EXAMPLES

The disclosure and its advantages are illustrated hereinafter in examples.

Example 1: Production of Methanethiol from Methanol, in the Presence of a Catalyst Based on Mixed Oxides, According to the Invention Preparation of the Catalyst Cat1 With the Composition LaCeNdZr (2/21.3/5.1/71.6)

The catalyst has been prepared through soft chemistry synthesis routes. For example, it could be obtained according to the method described in the patent FR2907445A1 or the patent FR2859470A1. The specific surface area of this catalyst is 75 $m^2 \cdot g^{-1}$. The composition of oxides in weight percent is 2.0% of $La_2O_3$, 21.3% of $CeO_2$, 5.1% of $Nd_2O_3$ and 71.6% of $ZrO_2$.

Production of Methanethiol by Hydrosulfurization of Methanol in the Presence of the Catalyst Hereinabove A catalytic bed of 2 ml of catalyst diluted in carborundum with a grain-size distribution comprised between 0.400 and 0.500 nm is placed in a reaction with a 1.26 cm internal diameter. The inlet gases of the reactor are constituted by a mixture of methanol and hydrogen sulfide.

Different operational conditions are tested and described hereinbelow:

1) molar ratio $H_2S$/MeOH=0.5/temperature=330° C./contact time=10 s
2) molar ratio $H_2S$/MeOH=4/temperature=375° C./contact time=20 s
3) molar ratio $H_2S$/MeOH=1.7/temperature=400° C./contact time=4 s.

The pressure in the reactor is 10 bars.

In order to compare the performances of a method of the disclosure with a method of the prior art, the same reaction is performed in the same conditions in the presence of a catalyst constituted by cerium oxide (with a specific surface area 99 $m^2 \cdot g^{-1}$) similar to that one described in the prior art.

The results are reported in Table 1 hereinbelow:

TABLE 1

| Operational conditions | Catalyst | Conversion (%) | Selectivities (%) | | | | |
|---|---|---|---|---|---|---|---|
| | | | $CH_3SH$ | $(CH_3)_2S$ | $(CH_3)2O$ | Light gases* | $CH_3SH$ + $(CH_3)_2S$ |
| 1 | Ceria | 16.2 | 84.1 | 6.7 | 3.2 | 6.0 | 90.8 |
| | Cat1 | 17.1 | 85.9 | 8.0 | 5.2 | 1.0 | 93.9 |
| 2 | Ceria | 92.8 | 73.7 | 13.3 | 0.1 | 12.7 | 77.0 |
| | Cat1 | 95.7 | 84.5 | 13.1 | 0.2 | 1.7 | 97.6 |
| 3 | Ceria | 58.8 | 81.0 | 8.8 | 0.8 | 9.3 | 89.8 |
| | Cat1 | 55.8 | 80.8 | 12.6 | 2 | 3.8 | 93.4 |

*CO, $CO_2$ and $CH_4$

It is observed that, regardless of the conditions, the method of the disclosure features both a greater methanol conversion and a higher methanethiol selectivity, while producing very small amounts of light gases to the benefit of a greater dimethyl sulfide selectivity. These results highlight the performances of a catalyst engaged in a method according to the disclosure in comparison with ceria. They further demonstrate that in order to reach an optimum methanethiol production, it is advantageous that the method includes a complementary step in which the produced dimethyl sulfide is converted into methanethiol, in the presence of a catalyst known to those skilled in the art, such as an alumina.

Example 2: Production of Methanethiol from Methanol, in the Presence of a Catalyst Based on Mixed Oxides, According to the Invention Preparation of the Catalyst Cat2 with the Composition LaCeNdZr (1.75/30.3/5.35/62.6)

The catalyst Cat2 is prepared according to the same technique as the catalyst Cat1 hereinabove. The specific surface area of this catalyst is 59 $m^2 \cdot g^{-1}$. The composition of oxides in weight percent is 1.75% of $La_2O_3$, 30.3% of $CeO_2$, 5.35% of $Nd_2O_3$ and 62.6% of $ZrO_2$.

Production of Methanethiol by Hydrosulfurization of Methanol in the Presence of the Catalyst Hereinabove The catalytic performances of this catalyst have been determined in the same experimental system as Example 1, with a molar ratio $H_2S/MeOH$=1.7, a temperature of 375° C. and a pressure in the reactor of 10 bars.

The performances of the catalysts have been compared over a wide range of methanol conversions by varying the introduced catalyst mass and the flow rate of the different reactants.

The results are reported in Table 2 hereinbelow:

TABLE 2

| Conversion (%) | Catalyst | Selectivities (%) | | | | |
|---|---|---|---|---|---|---|
| | | $CH_3SH$ | $(CH_3)_2S$ | $(CH_3)_2O$ | Light gases* | $CH_3SH + (CH_3)2S$ |
| 20 | Ceria | 91.5 | 4.3 | 1.6 | 2.5 | 95.8 |
| | Cat2 | 92.7 | 3.4 | 2.1 | 1.6 | 96.1 |
| 40 | Ceria | 86.8 | 7.5 | 0.6 | 5.0 | 94.3 |
| | Cat2 | 90.1 | 6.9 | 1.6 | 1.2 | 97.0 |
| 60 | Ceria | 74.3 | 13.5 | 0.6 | 11.7 | 77.8 |
| | Cat2 | 81.3 | 14.7 | 1.3 | 2.4 | 96.0 |
| 80 | Ceria | 72.0 | 13.7 | 0.3 | 14.0 | 75.7 |
| | Cat2 | 70.1 | 24.2 | 1.1 | 4.4 | 94.3 |

*CO, $CO_2$ and $CH_4$

Example 3: Production of Methanethiol From Methanol, in the Presence of a Catalyst Based on a Cerium Oxide, Supported on a Modified Alumina, According to the Invention Preparation of the Catalyst CatS3 Supported on Alumina Modified by Potassium The supported catalyst CatS3 is synthesized by successive impregnations and calcinations (450° C. in air) of 100 g of commercial alumina with a specific surface area of 171 $m^2 \cdot g^{-1}$ by a solution of potassium hydroxide (38 g/L), and then by a solution of cerium (III) nitrate (1151 g/L). The potassium content is 1.5 weight %, the cerium oxide content is 3.5 weight %. The specific surface area of the catalyst is 167 $m^2 \cdot g^{-1}$.

Production of Methanethiol by Hydrosulfurization of Methanol in the Presence of the Catalyst Hereinabove The catalytic performances of these catalysts have been determined in experimental conditions identical to Example 2.

In order to compare the performances of a method of the disclosure with a method of the prior art, the same reaction is performed in the same conditions in the presence of the same pure alumina used as a support of CatS3 and of a catalyst (KS) constituted by potassium and supported by this same aforementioned alumina, synthesized according to the method described for the catalyst CatS3. The performances of the catalysts have been compared over a wide range of methanol conversions by varying the introduced catalyst mass and the flow rate of the different reactants.

The results are reported in Table 3 hereinbelow:

TABLE 3

| Catalyst | Conversion (%) | Selectivities (%) | | | | |
|---|---|---|---|---|---|---|
| | | $CH_3SH$ | $(CH_3)_2S$ | $(CH_3)_2O$ | Light gases* | $CH_3SH + (CH_3)_2S$ |
| Alumina | 84.1 | 47.5 | 37.9 | 14.6 | 0.1 | 85.4 |
| KS | 20.0 | 78.4 | 2.2 | 19.0 | 0.4 | 80.6 |
| CatS3 | 26.3 | 92.9 | 2.2 | 4.2 | 0.4 | 95.1 |
| | 40.1 | 93.3 | 3.2 | 3.2 | 0.2 | 96.5 |
| | 58.6 | 90.1 | 6.3 | 2.6 | 0.6 | 96.4 |
| | 76.6 | 83.4 | 12.6 | 2.1 | 1.6 | 96.0 |

*CO, $CO_2$ and $CH_4$

These results demonstrate the effectiveness of ceria supported on a modified alumina, in particular impregnated beforehand with potassium.

The invention claimed is:

1. A method for preparing a compound of formula RSH where R represents an alkyl group, by gas-phase catalytic reaction of hydrogen sulfide with a compound of formula ROH, in the presence of a solid catalyst, characterized in that the reaction is performed in the presence of a catalyst which consists of cerium oxide and is supported within ranges comprised between 0.1% and 50% (m/m), on an alumina impregnated with potassium whose content is comprised between 0.1% and 20% (m/m).

2. The preparation method according to claim 1, wherein the compound of formula RSH is methanethiol and is prepared by catalytic hydrosulfurization of methanol in a gas phase by reaction with hydrogen sulfide.

3. The preparation method according to claim 1, wherein the molar ratio between the hydrogen sulfide and the compound ROH is comprised between 0.5 and 20.

4. The preparation method according to claim 1, wherein the reaction is performed at a temperature comprised between 200° C. and 450° C., advantageously under a pressure comprised between 2 and 20 bar, and the contact time of the compound ROH with the catalyst is comprised between 0.1 second and 60 seconds.

5. The preparation method according to claim 1, wherein the reaction produces dimethyl sulfide and in that a catalytic conversion reaction of said dimethyl sulfide into methanethiol is further performed.

* * * * *